United States Patent [19]
Long et al.

[11] Patent Number: 5,961,514
[45] Date of Patent: Oct. 5, 1999

[54] CORDLESS ELECTROSURGICAL INSTRUMENT

[75] Inventors: Gary L. Long, Cincinnati; Lynetta J. Freeman, West Chester; Bryan D. Knodel, Cincinnati, all of Ohio

[73] Assignee: Ethicon Endo-Surger, Inc., Cincinnati, Ohio

[21] Appl. No.: 08/877,715

[22] Filed: Jun. 18, 1997

Related U.S. Application Data

[63] Continuation-in-part of application No. 08/856,534, May 14, 1997.

[51] Int. Cl.⁶ .................................................. A61B 17/39
[52] U.S. Cl. ............................... 606/41; 606/48; 606/51
[58] Field of Search ......................... 606/41, 45–52

[56] References Cited

U.S. PATENT DOCUMENTS

| | | | |
|---|---|---|---|
| 1,620,929 | 3/1927 | Wallerich . | |
| 4,535,773 | 8/1985 | Yoon | 604/51 |
| 4,674,010 | 6/1987 | van den Steen | 361/433 |
| 4,717,438 | 1/1988 | Benge et al. | 156/152 |
| 4,799,480 | 1/1989 | Abraham et al. | 128/303.13 |
| 4,825,217 | 4/1989 | Choi | 343/715 |
| 4,884,982 | 12/1989 | Fleming et al. | 439/620 |
| 4,934,960 | 6/1990 | Capp et al. | 439/620 |
| 4,936,842 | 6/1990 | D'Amelio et al. | 606/42 |
| 5,105,829 | 4/1992 | Fabian et al. | 128/899 |
| 5,207,691 | 5/1993 | Nardella | 606/142 |
| 5,273,524 | 12/1993 | Fox et al. | 604/21 |
| 5,342,356 | 8/1994 | Ellman et al. | 606/32 |
| 5,342,357 | 8/1994 | Narella | 606/40 |
| 5,344,420 | 9/1994 | Hilal et al. | 606/28 |
| 5,354,291 | 10/1994 | Bales et al. | 604/35 |
| 5,380,321 | 1/1995 | Yoon | 606/41 |
| 5,383,860 | 1/1995 | Lau | 604/167 |
| 5,387,196 | 2/1995 | Green et al. | 604/158 |
| 5,387,197 | 2/1995 | Smith et al. | 604/164 |
| 5,391,166 | 2/1995 | Eggers | 606/48 |
| 5,401,274 | 3/1995 | Kusunoki | 606/41 |
| 5,403,312 | 4/1995 | Yates et al. | 606/50 |
| 5,417,687 | 5/1995 | Nardella et al. | 606/32 |
| 5,432,486 | 7/1995 | Wong | 333/109 |
| 5,437,277 | 8/1995 | Dumoulin et al. | 128/652.1 |
| 5,443,462 | 8/1995 | Hannant | 606/34 |
| 5,445,142 | 8/1995 | Hassler, Jr. | 600/105 |
| 5,445,638 | 8/1995 | Rydell et al. | 606/51 |
| 5,449,355 | 9/1995 | Rhum et al. | 606/41 |
| 5,540,684 | 7/1996 | Hassler, Jr. | 606/40 |
| 5,545,142 | 8/1996 | Stephens et al. | 604/167 |
| 5,562,611 | 10/1996 | Transue | 604/26 |
| 5,571,100 | 11/1996 | Goble et al. | 606/41 |
| 5,573,535 | 11/1996 | Viklund | 606/51 |
| 5,591,192 | 1/1997 | Privitera et al. | 606/185 |
| 5,597,107 | 1/1997 | Knodel et al. | 227/175.2 |
| 5,599,348 | 2/1997 | Gentelia et al. | 606/45 |
| 5,658,279 | 8/1997 | Nardella et al. | 606/45 |
| 5,733,323 | 3/1998 | Buck et al. | 607/122 |

*Primary Examiner*—Linda C. M. Dvorak
*Assistant Examiner*—Roy Gibson
*Attorney, Agent, or Firm*—Bernard Shay

[57] ABSTRACT

An improved electrosurgical instrument for use with a specially adapted electrosurgical trocar. The improved electrosurgical instrument including a handle, an end effector and an elongated closure tube connecting the handle to the end effector. The elongated closure tube including one or more electrical contacts adapted to provide electrical contact to the interior of a trocar cannula as the electrosurgical instrument is passed through the cannula. The contacts being electrically connected to the end effector of the electrosurgical instrument such that electrosurgical energy passes through the contacts to the end effector.

3 Claims, 9 Drawing Sheets

FIG. 11

CORDLESS ELECTROSURGICAL INSTRUMENT

This is a continuation-in-part of application Ser. No. 08/856,534, filed May 14, 1997, which is hereby incorporated herein by reference.

FIELD OF THE INVENTION

The present invention relates, in general, to an improved electrosurgical instrument and method of use and, more particularly, to a cordless electrosurgical instrument adapted to receive electrosurgical energy from a specially adapted electrosurgical trocar.

BACKGROUND OF THE INVENTION

The surgical trocar has become the mainstay in the development and acceptance of endoscopic surgical procedures. Endoscopic surgery involves the performance of surgery through a number of openings having a relatively small diameter. These openings are made with the trocar, which typically includes a trocar obturator and a trocar cannula. The obturator is the piercing implement which punctures the body wall to make the opening. Once the puncture is made, the obturator is withdrawn from the cannula. The cannula then provides a small diameter passageway into and through the body wall to provide access for additional surgical instrumentation to the surgical site. The function, structure and operation of a typical trocar is described in detail in U.S. Pat. No. 5,387,197, which is hereby incorporated herein by reference.

Such additional surgical instruments may include, for example, bipolar or monopolar electrosurgical instruments which utilize radio frequency electrosurgical energy. Known electrosurgical instruments include, for example, bipolar forceps, bipolar scissors, monopolar-hook, monopolar-scissors and, bipolar endocutters. Each of those instruments has an electrosurgical end effector which is adapted to treat tissue through the application of electrosurgical (e.g. radio frequency or RF) energy to tissue which is brought in contact with the electrosurgical end effector. Most known electrosurgical instruments are connected by electrical cords to electrosurgical generators. The structure and operation of a typical mechanical cutter/stapler is described in U.S. Pat. No. 5,597,107 which is hereby incorporated herein by reference. The structure and operation of a typical bipolar cutter/stapler ("bipolar endocutter") is described in U.S. Pat. No. 5,403,312 which is hereby incorporated herein by reference.

Electrosurgical generators, such as the Force II generator which is available from Valley Lab of Bolder Colo., supply electrical energy to the electrosurgical instruments through electrical cords. The electrical cords, being attached directly to the electrosurgical instrument, may make the electrosurgical instrument inconvenient to use. Alternatively, electrical cords may cause undesirable delays as one electrosurgical instrument is unplugged from the generator and another is plugged in. Thus, it would be advantageous to design a cordless electrosurgical instrument which is adapted to be connected to an electrosurgical generator through a specially designed trocar or a trocar adapter.

SUMMARY OF THE INVENTION

In the present invention, a cordless electrosurgical instrument is adapted to receive electrosurgical energy from a specially designed trocar or trocar adapter. In one embodiment of the present invention, an electrosurgical instrument includes a handle, an elongated tube and an electrosurgical end effector. The handle may include an actuator such as a trigger which is operatively connected to the end effector through the elongated tube. The elongated tube may be a closure tube which is adapted to close the end effector when the handle actuator is moved. Alternatively, the closure tube may include a mechanism connecting the handle actuator to the end effector, which mechanism acts to close the end effector when the handle actuator is moved. The electrosurgical end effector is adapted to apply electrosurgical energy to biological tissue in order to effect treatment of the tissue. The elongated closure tube includes one or more electrical contacts adapted to couple electrosurgical energy to the end effector. The electrical contacts are connected to the end effector through one or more electrical conductors.

In one embodiment of the present invention, the elongated closure tube is electrically conductive and includes an insulation region and one of the electrical contacts passes through the insulation region from the interior of the elongated closure tube to the outer surface of the elongated closure tube. In a further embodiment of the invention, the electrical contacts are raised above the surface of the elongated tube. In a further embodiment of the present invention, the second electrical contact may be electrically connected to the elongated closure tube. The elongated conductive closure tube may also include an insulator positioned on the exterior of the tube, with a hole through the tube for the first electrode.

In a further embodiment of the present invention, the electrosurgical instrument according to the present invention is adapted to fit through an trocar which includes an electrosurgical adapter with at least a first electrical contact positioned in and extending axially along the elongated aperture, at least a first electrical conductors, at least a first external conductor, a compression mechanism, an outer housing and an electrical cord.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
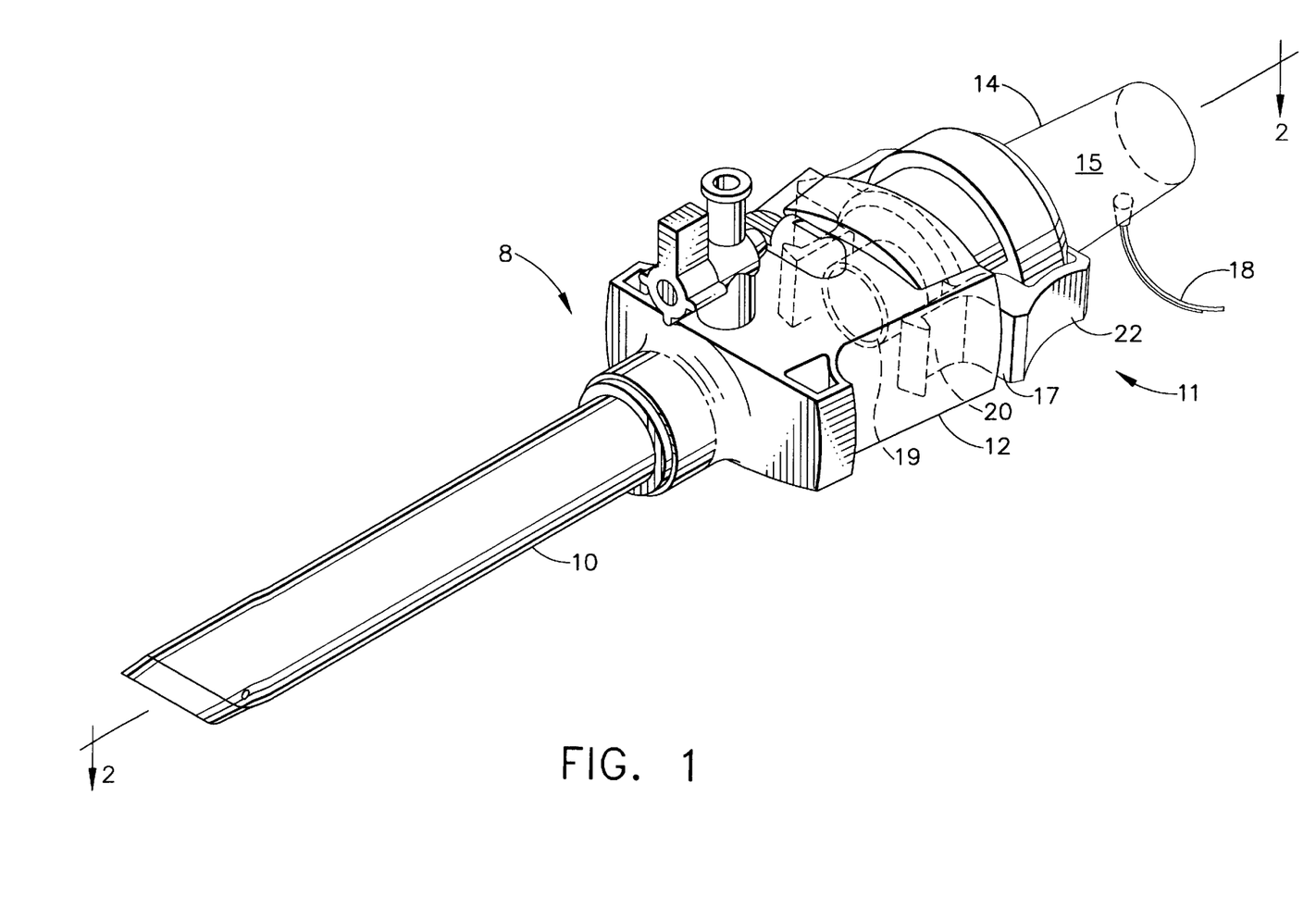
FIG. 1 is a perspective view of an electrosurgical trocar according to the present invention.

FIG. 1 is a perspective view of an electrosurgical trocar according to the present invention. Electrosurgical trocar 11 includes trocar cannula 8 and electrosurgical adapter 14. Electrosurgical trocar 11 may also include an obturator assembly (not shown) such as the one illustrated in U.S. Pat. No. 5,387,197, which has been previously incorporated herein by reference. Trocar cannula 8 includes cannula housing 12 and cannula tube 10, extending from housing 12. Electrosurgical adapter 14 includes an adapter housing 15, locking connector 17 and an electric cord 18. In the embodiment of the invention illustrated in FIG. 1, electrosurgical adapter 14 is connected to trocar cannula 8 by locking connector 17. Locking connector 17 includes locking cleat 20 and release button 22. It will be apparent that electrosurgical adapter 14 may be integrated directly into trocar cannula 8, thus eliminating the need for locking connector 17.

Figure 2:
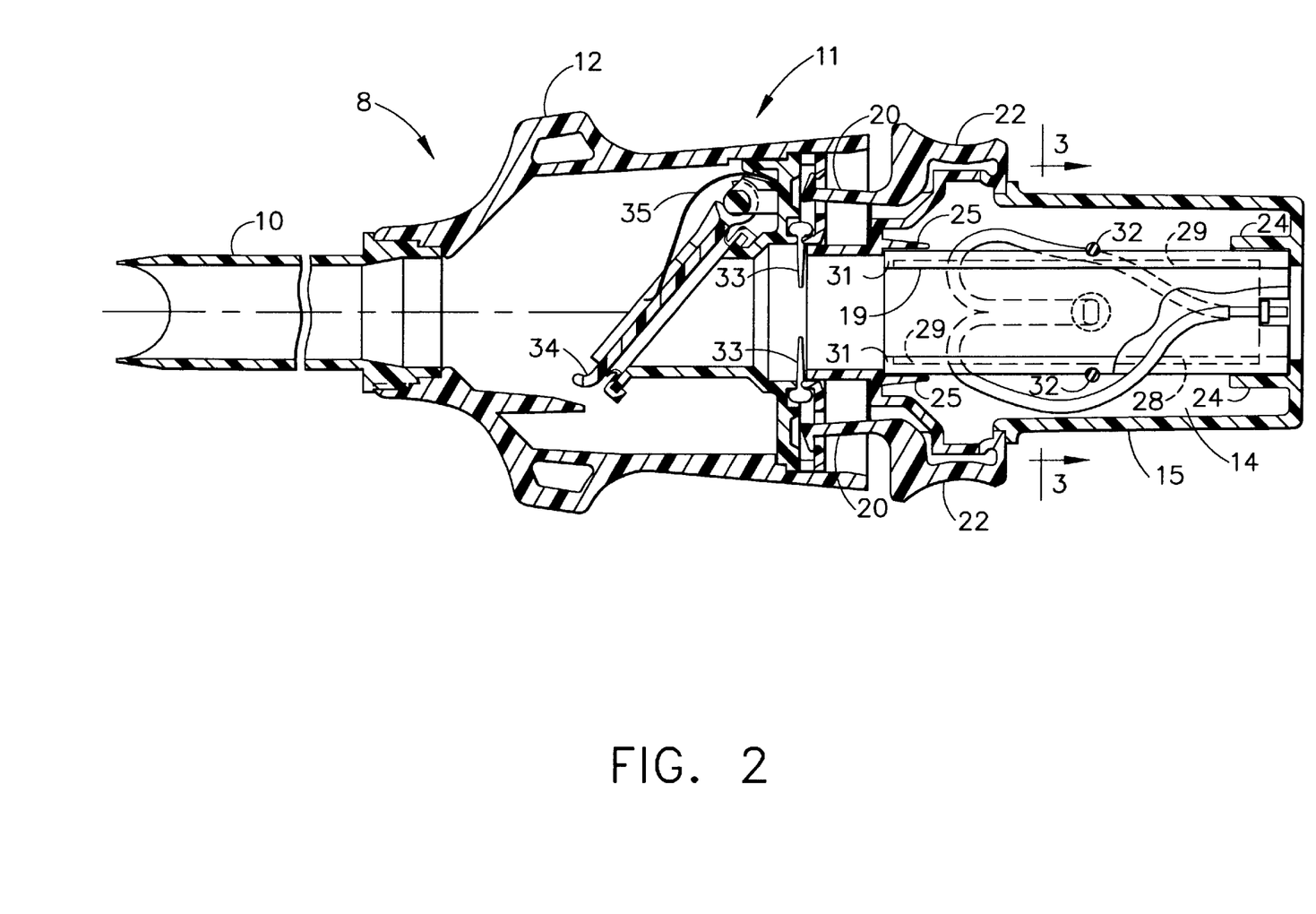
FIG. 2 is a plane view section taken through the electrosurgical trocar illustrated in FIG. 1.

FIG. 2 is a plane view section taken through electrosurgical trocar 11. In FIG. 2, cannula housing 12 includes flapper valve 34 and ring gasket 33. Electrosurgical adapter 14 includes central aperture 19, front flange 25 and base flange 24. Aperture 19 is an elongated aperture for receiving working instruments such as endoscopic electrosurgical instruments. Electrosurgical adapter 14 further includes one or 17 electrical contacts which, in the embodiment illustrated in FIGS. 2 and 3, comprise stator plates 28 and 29. At least a portion of the interior wall of central aperture 19 is formed by upper insulator 30 and upper stator plate 28. Upper insulator 30 is positioned against front flange 25 and base flange 24. Compression member 32 is, in the present embodiment, an o-ring which is positioned outside of upper insulator 30 to bias upper insulator 30 and upper stator plate 28 toward the center of central aperture 19. Compression member 32 may also be, for example, a spring, a flexible sleeve, a plurality of o-rings or any other suitable biasing member.

Figure 3:
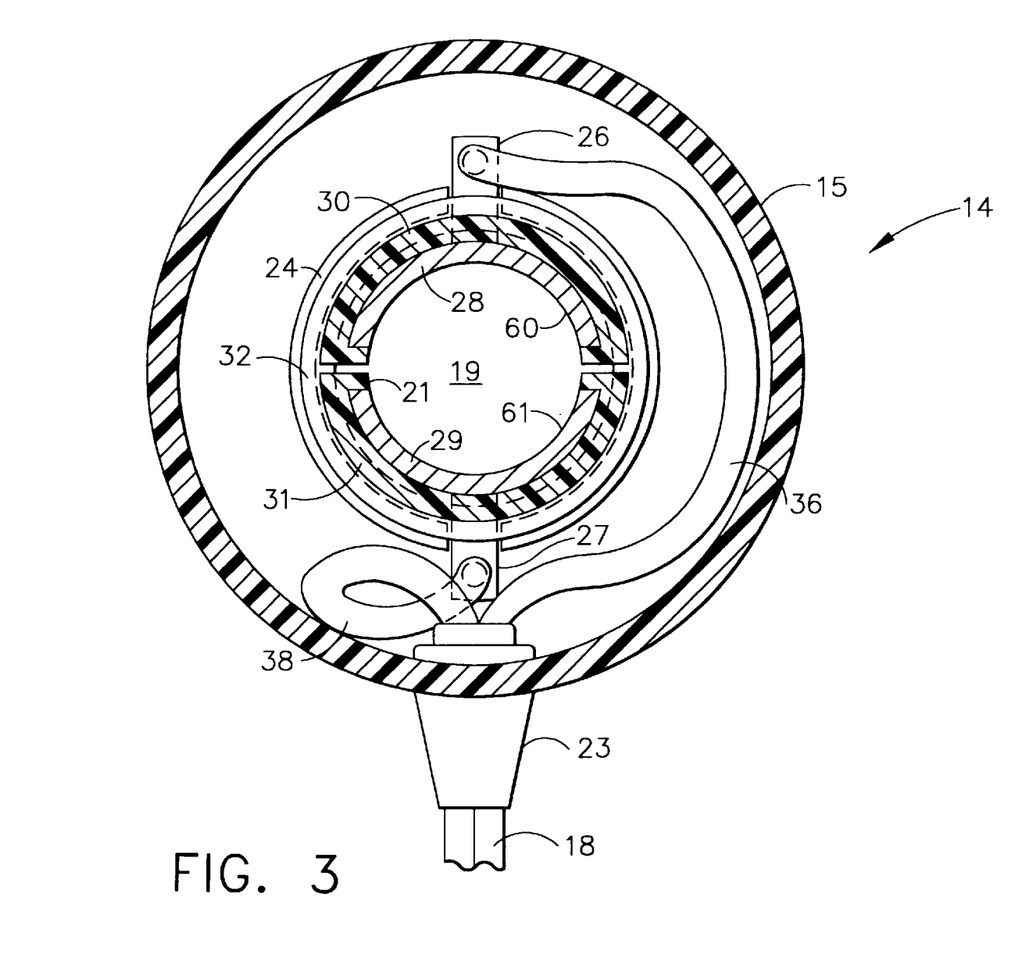
FIG. 3 is a section view taken along line 3—3 of FIG. 2.

FIG. 3 is a sectional view of electrosurgical adapter 14 taken along line 3—3 of FIG. 2. Central aperture 19 is defined by aperture interior wall 21. The portion of interior wall 21 visible in FIG. 3 is formed, at least in part, by upper contact surface 60 of upper stator plate 28 and lower contact surface 61 of lower stator plate 29. Upper stator plate 28 and lower stator plate 29 are positioned on, and electrically insulated from one another by, upper insulator 30 and lower insulator 31, respectively. Compression member 32 surrounds upper insulator 30 and lower insulator 31. Compression member 32, which is an o-ring in the embodiment of FIGS. 2–3, biases upper insulator 30 and lower insulator 31 toward the center of central aperture 19. Electric cord 18 is connected to upper stator plate 28 by upper conductor 36 and upper stator tab 26. Electric cord 18 is connected to lower stator plate 29 by lower conductor 38 and lower stator tab 27. Base flange 24, which is part of adapter housing 15, holds upper insulator 30 and lower insulator 31 in place. Strain relief 23 protects electric cord 18 as it passes through adapter housing 15.

Figure 4:
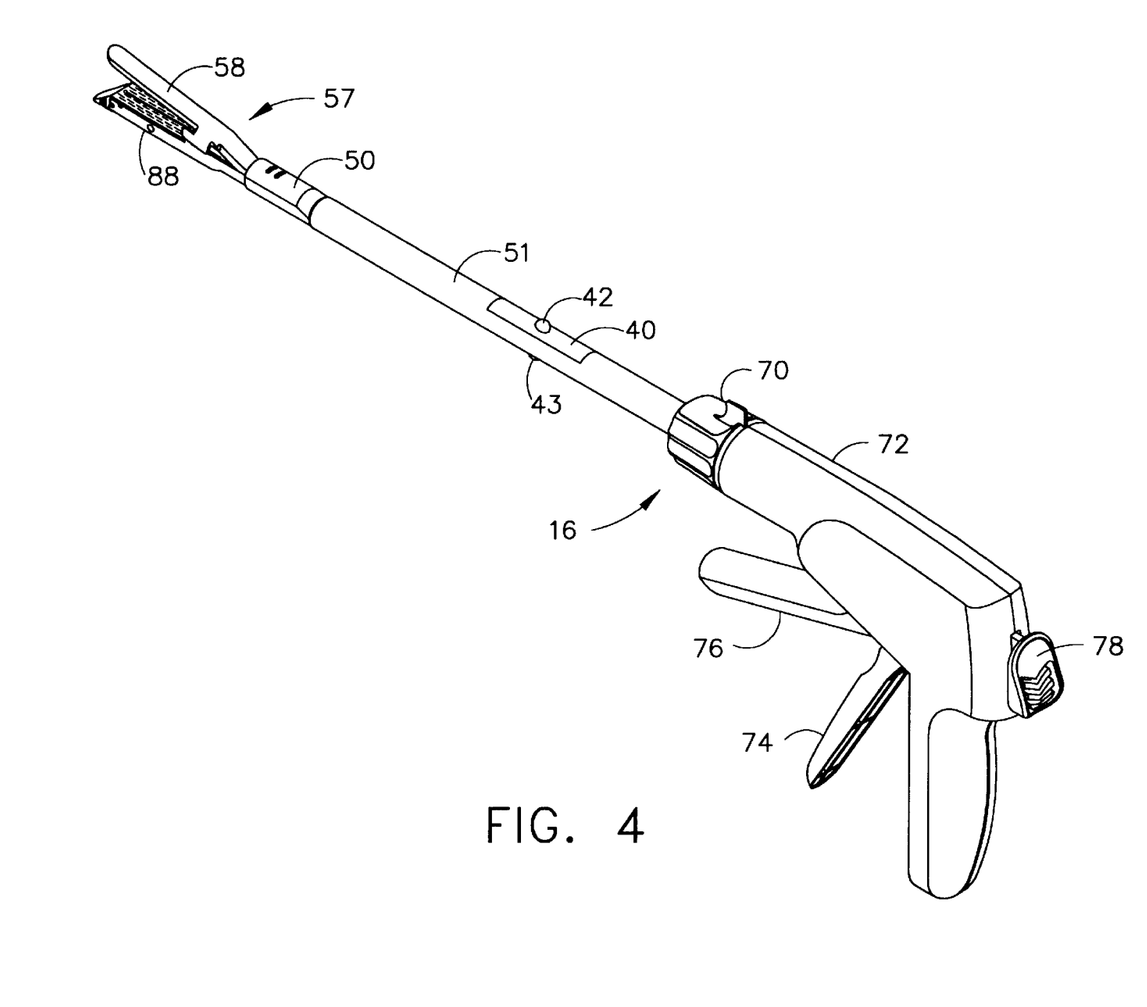
FIG. 4 is a perspective view of a cordless bipolar electrosurgical instrument according to the present invention.

FIG. 4 is a perspective view of a cordless electrosurgical instrument which may be, for example, a bipolar cutter/stapler. In FIG. 4, electrosurgical instrument 16 includes handle 72, closure tube 50 and end effector 57 which, in the embodiment illustrated in FIG. 4 is a bipolar cutter/stapler. Alternative bipolar end effectors may include: a bipolar forceps such as the forceps illustrated in U.S. Pat. No. 5,540,684 a bipolar cutting an coagulation instrument such as the tissue cutting forceps illustrated in U.S. Pat. No. 5,445,638; a bipolar scissors such as the shears illustrated in U.S. Pat. No. 5,352,222; or a bipolar probe such as the probe illustrated in U.S. Pat. No. 5,342,357. U.S. Pat. Nos. 5,540,684 5,445,638, 5,352,222 and 5,342,357 are hereby incorporated herein by reference. Closure tube 50 is elongated to facilitate insertion of end effector 57 through a trocar cannula, such as cannula 8 of trocar 11 thus facilitating the use of electrosurgical instrument 16 in endoscopic or laparoscopic surgical procedures. Closure tube 50 may be any appropriate shape, including, for example, an elongated square or triangular tube. Handle 72, which is located at the proximal end of instrument 16, includes grasping trigger 74, firing trigger 76 and release trigger 78. Closure tube 50, which connects handle 72 to end effector 57, includes rotation knob 70, first contact insulator 40, first instrument electrode contact 42, second instrument electrode contact 43 and outer tube 51. End effector 57, which is located at the distal end of closure tube 50 includes anvil 58 and cartridge channel 88. Electrosurgical instrument 16 is similar in structure and operation to the bipolar endoscopic electrocautery linear cutting and stapling instrument illustrated and described in U.S. Pat. No. 5,403,312, which has been previously incorporated herein by reference. However electrosurgical instrument 16 is cordless. In electrosurgical instrument 16, electrosurgical energy is supplied to the instrument through first instrument electrode contact 42 and second instrument electrode contact 43.

Figure 5:
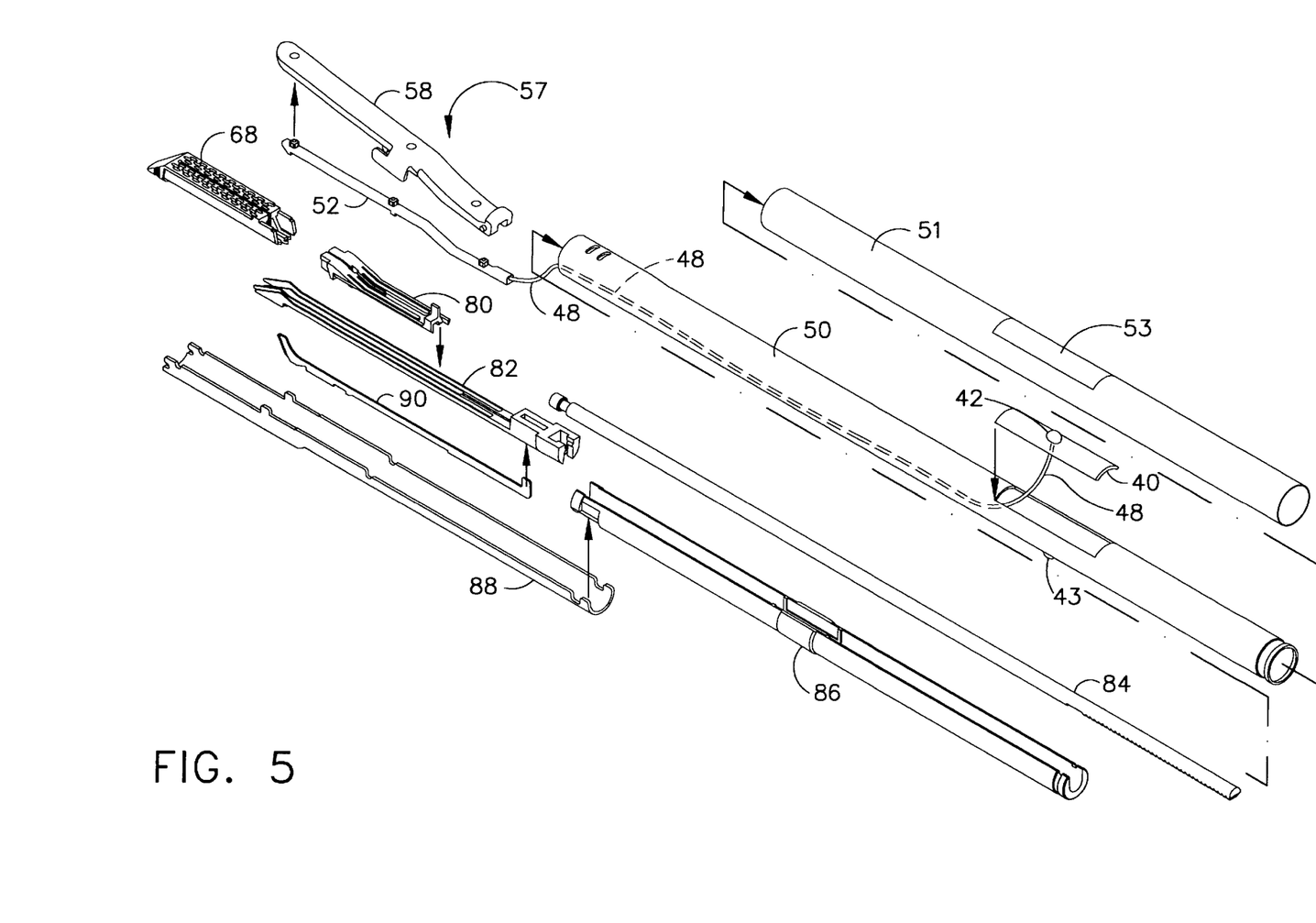
FIG. 5 is an exploded perspective view of the distal end of a cordless electrosurgical instrument according to the present invention.

FIG. 5 is an exploded perspective view of the distal end of an electrosurgical instrument according to the present invention, such as electrosurgical instrument 16. In FIG. 5, outer tube 51 is positioned over closure tube 50. In the instruments illustrated in FIGS. 4 and 5, closure tube 50 is electrically conductive and outer tube 51 is constructed of an electrically insulating material. First instrument electrode contact 42, which penetrates first contact insulator 40, extends through opening 53 in outer tube 51. First contact insulator 40 electrically isolates instrument electrode contact 42 from closure tube 50. Second instrument electrode contact 43, which is connected to and in electrical contact with closure tube 50, extends through a second opening (not shown) in outer tube 51. In an alternate electrosurgical instrument, contact 43 could be connected to an electrode on end effector 57 by an insulated wire which runs through closure tube 50 and, in such an instrument, closure tube 50 may be constructed of an insulating material. In a further alternative embodiment of the present invention, for use in a monopolar electrosurgical instrument, contact 43 may be eliminated. In such an instrument, as in other monopolar instruments, the return path for the electrosurgical energy may be provided by a conductive pad affixed to the skin of the patient. In FIG. 5, Conductor 48 passes through closure tube 51 from first instrument electrode contact 42 to electrode assembly 52, electrically connecting contact 42 to electrode assembly 52. Electrode assembly 52 is positioned in anvil 58. Electrode assembly 52 may be electrically insulated from anvil 58 and closure tube 50 to prevent electrode assembly 52 from shorting to anvil 58 or closure tube 50. Conductor 48 may be insulated to prevent it from shorting to closure tube 50 or any of the mechanisms in closure tube 50.

Figure 6:
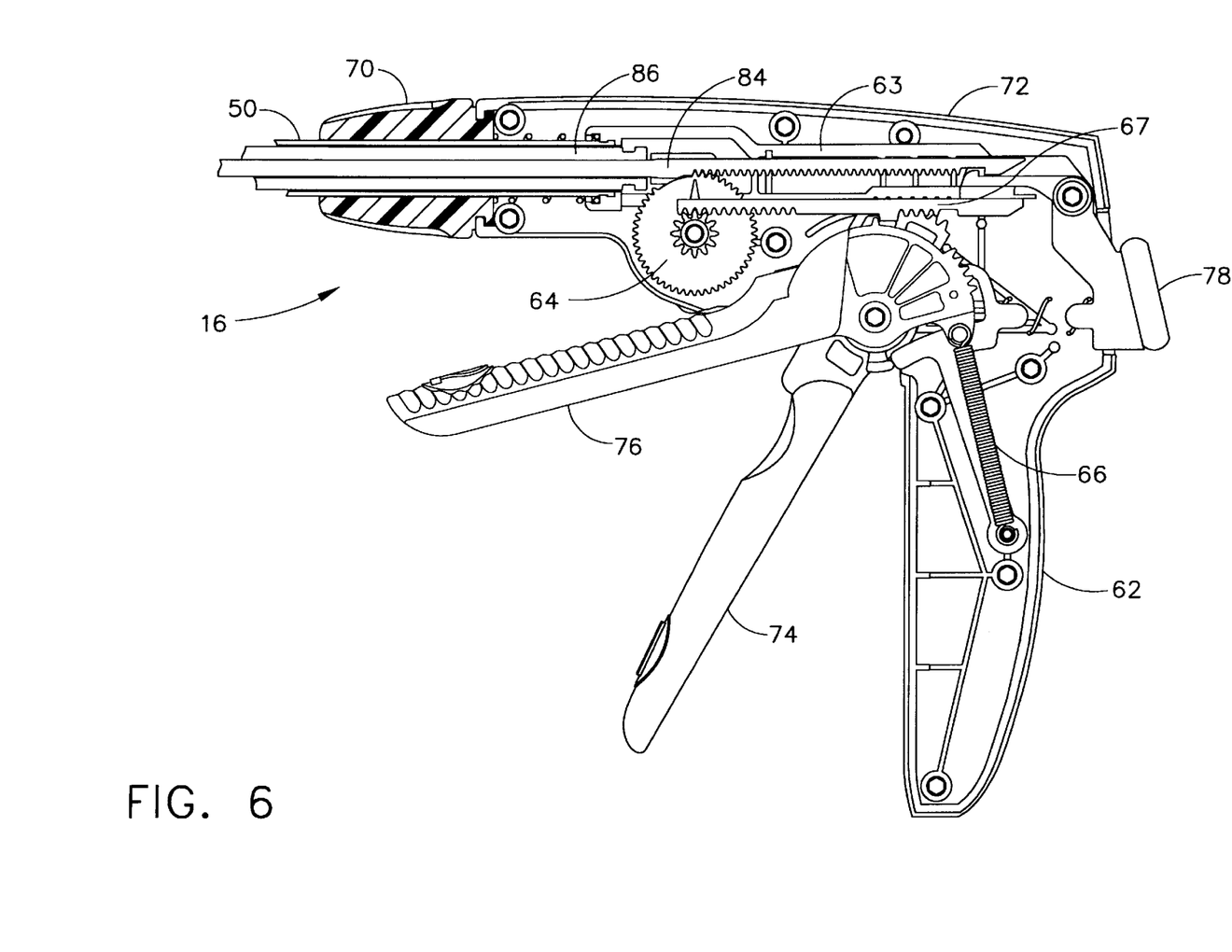
FIG. 6 is a cut away view of the handle of the electrosurgical instrument illustrated in FIG. 4.

FIG. 6 is a cut away view of the handle of electrosurgical instrument 16 illustrated in FIG. 4. In FIG. 6, handle 72 includes grip 62, grasping trigger 74 and firing trigger 76. Pivotal movement of grasping trigger 74 results in distal movement of yoke 63 and closure tube 50, closing anvil 58 against staple cartridge 68 which is positioned in cartridge channel 88. Pivotal movement of grasping trigger 74 further releases firing rod 84 and positions firing trigger 76 to engage drive member 67. Further pivotal movement of firing trigger 76 toward grip 62 results in distal movement of drive member 67 which rotates multiplier 64 in a counterclockwise direction. Counterclockwise rotation of multiplier 64 results in distal movement of firing rod 84 which, in the embodiment of the invention illustrated herein, fires the staples in staple cartridge 68.

In the cordless electrosurgical instruments illustrated in FIGS. 4–11, knife 90 is connected to wedge assembly 82 and wedge assembly 82 is connected to firing rod 84, which, in turn, is operatively connected to firing trigger 76. Closure tube 50 is operatively connected to rotation knob 70, grasping trigger 74 and release trigger 78. Wedge guide 80 is fitted over wedge block assembly 82 to guide wedge block assembly 82 as firing rod 84 moves wedge block assembly 82. The structure and operation of the mechanical features of the device illustrated in FIGS. 4–11 may be better understood with reference to the mechanical cutting and stapling instrument illustrated and described in U.S. Pat. No. 5,597,107 which is hereby incorporated herein by reference.

In the bipolar electrosurgical instrument illustrated in FIG. 4, cartridge channel 88 and outer tube 51 are electrically conductive and in electrical contact. Thus, in the embodiment of FIG. 4, anvil 58 includes an electrode assembly such as electrode assembly 52 which acts as a primary electrode while cartridge channel 88 acts as a second or return electrode. When electrically conductive tissue is grasped by end effector 57 and an electrosurgical generator is connected to first instrument electrode contact 42 and second instrument electrode contact 43, electrosurgical energy will flow through the grasped tissue, coagulating the grasped tissue.

Figure 7:
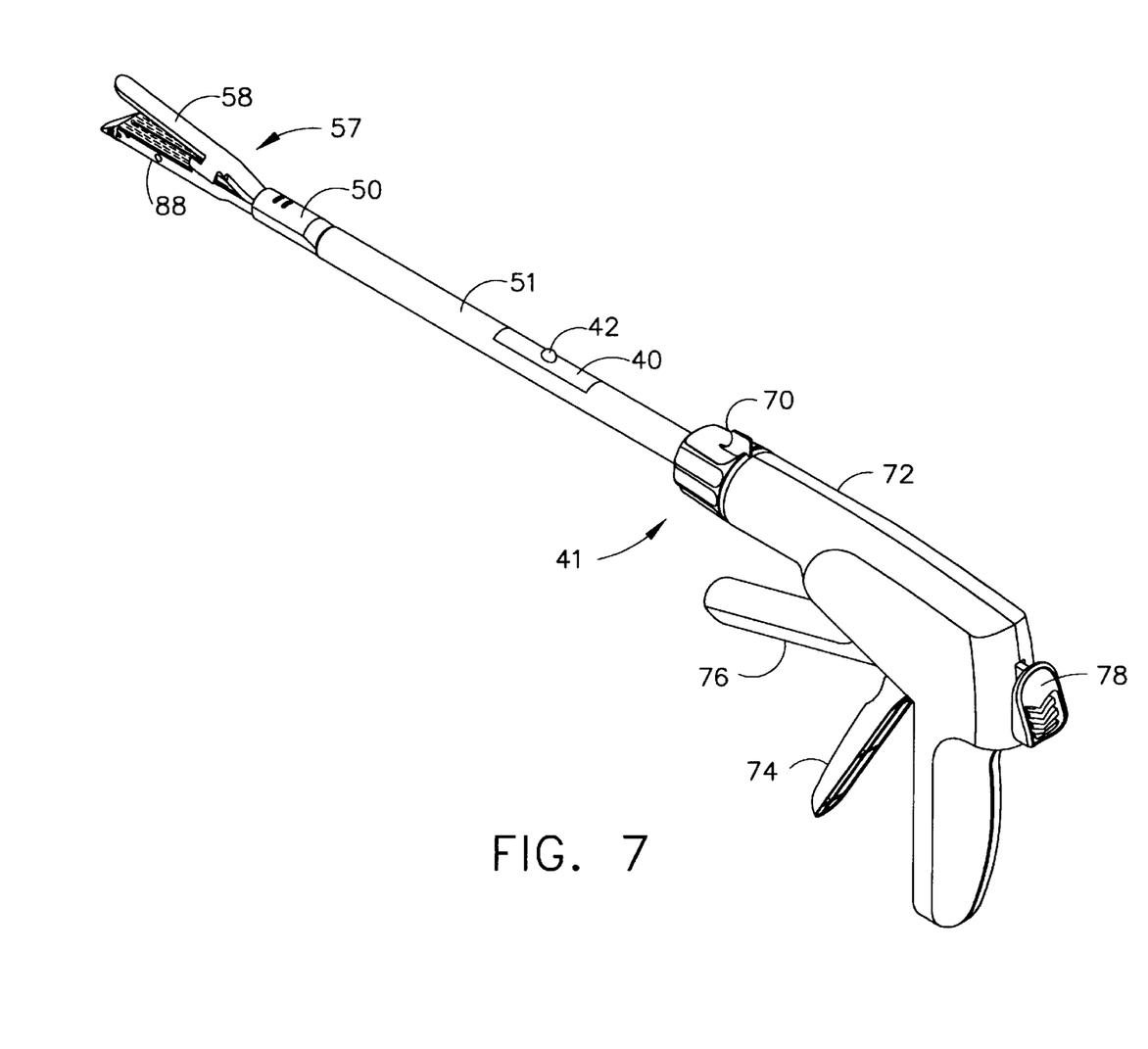
FIG. 7 is a perspective view of a cordless electrosurgical instrument according to the present invention.

FIG. 7 is a perspective view of a cordless monopolar electrosurgical instrument 41 which may be, for example, a monopolar cutter/stapler. Alternative monopolar end effectors may include, for example: a monopolar probe such as the probe illustrated in U.S. Pat. No. 5,273,524; or a monopolar electrosurgical clip applier such as the clip applier illustrated in U.S. Pat. No. 5,207,691. U.S. Pat. Nos. 5,273,524 and 5,207,691 are hereby incorporated herein by reference. In FIG. 7, electrosurgical instrument 41 includes handle 72, closure tube 50 and end effector 57. Closure tube 50 is elongated to facilitate insertion of end effector 57 through a trocar cannula, thus facilitating the use of electrosurgical instrument 41 in endoscopic or laparoscopic surgical procedures. Closure tube 50 may be any appropriate shape, including, for example, an elongated square or triangular tube. Handle 72, which is located at the proximal end of instrument 41, includes grasping trigger 74, firing trigger 76 and release trigger 78. Closure tube 50, which connects handle 72 to end effector 57, includes rotation knob 70, first contact insulator 40, instrument electrode contact 42 and outer tube 51. End effector 57, which is located at the distal end of closure tube 50 includes anvil 58 and cartridge channel 88 and may further include staple cartridge 68. Electrosurgical instrument 41 is similar in structure and operation to the endoscopic electrocautery linear cutting and stapling instrument illustrated and described in U.S. Pat. No. 5,403,312, which has been previously incorporated herein by reference except that electrosurgical instrument 41, as illustrated in FIG. 4, is adapted to work as a cordless monopolar instrument. In electrosurgical instrument 41, electrosurgical energy is supplied to the instrument through instrument electrode contact 42. In the monopolar instrument illustrated in FIG. 7, instrument electrode contact 42, which penetrates first contact insulator 40, and is connected to conductor 48 as illustrated in FIG. 5. Further, conductor 48 passes through closure tube 50 from instrument electrode contact 42 to electrode assembly 52, electrically connecting contact 42 to electrode assembly 52 as illustrated in FIG. 5. Electrode assembly 52 is positioned in anvil 58. Electrode assembly 52 may be electrically insulated from anvil 58 and closure tube 50 to prevent electrode assembly 52 from shorting to anvil 58 or closure tube 50. Conductor 48 may be insulated to prevent it from shorting to closure tube 50 or any of the mechanism in closure tube 50.

In the device illustrated in FIG. 7, electrode assembly 52 of FIG. 5 acts as a primary electrode and a secondary or return electrode is affixed to the skin of the patient. When electrically conductive tissue is grasped by end effector 57 and an electrosurgical generator is connected to first instrument electrode contact 42 and a second electrode is connected to the patient's skin, electrosurgical energy will flow through the grasped tissue to the external electrode, coagulating the grasped tissue.

Figure 8:
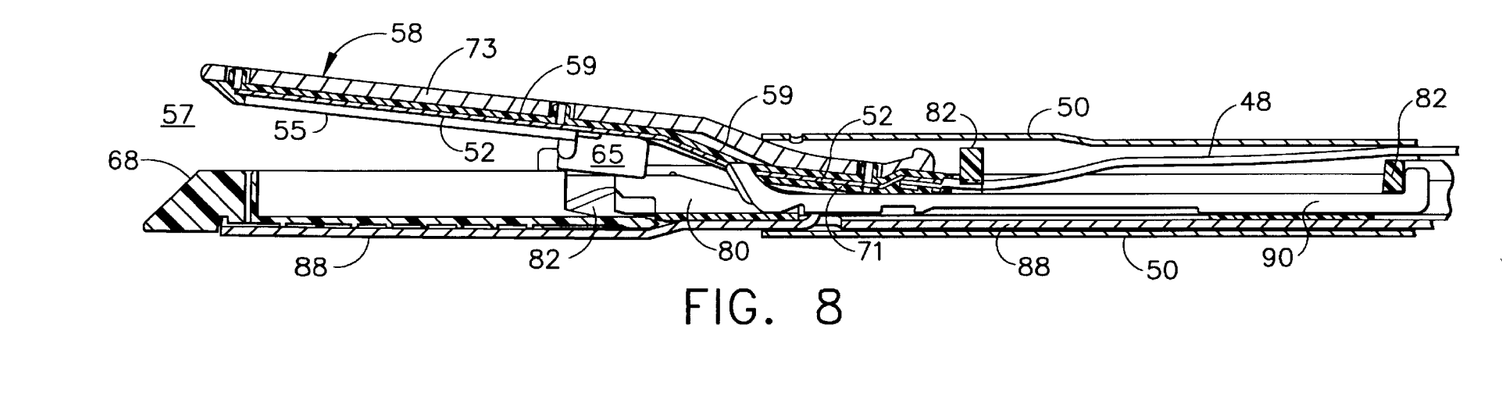
FIG. 8 is a cutaway view of an end effector of an electrosurgical instrument according to one embodiment of the present invention.
Figure 9:
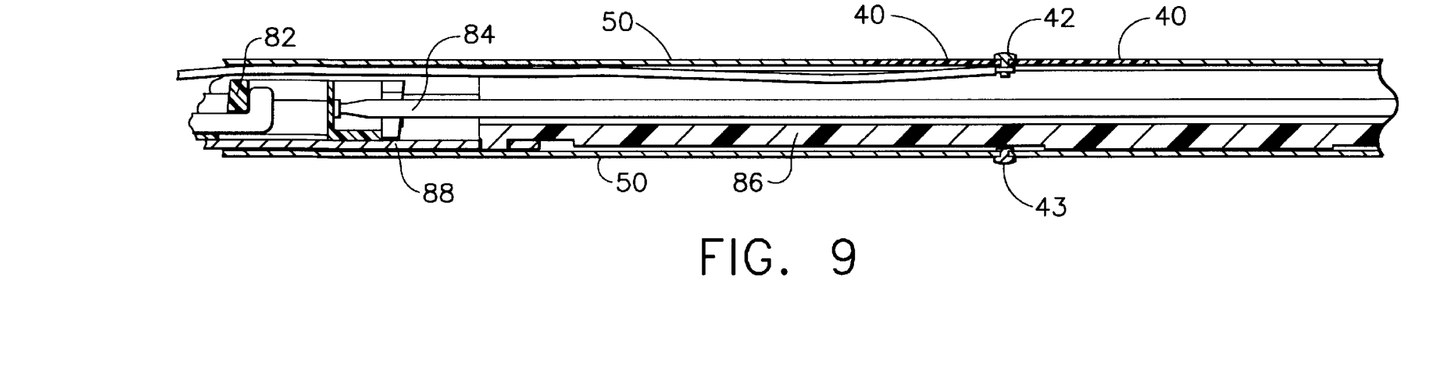
FIG. 9 is a cutaway view of a portion of a closure tube of an electrosurgical instrument according to one embodiment of the present invention.
Figure 10:
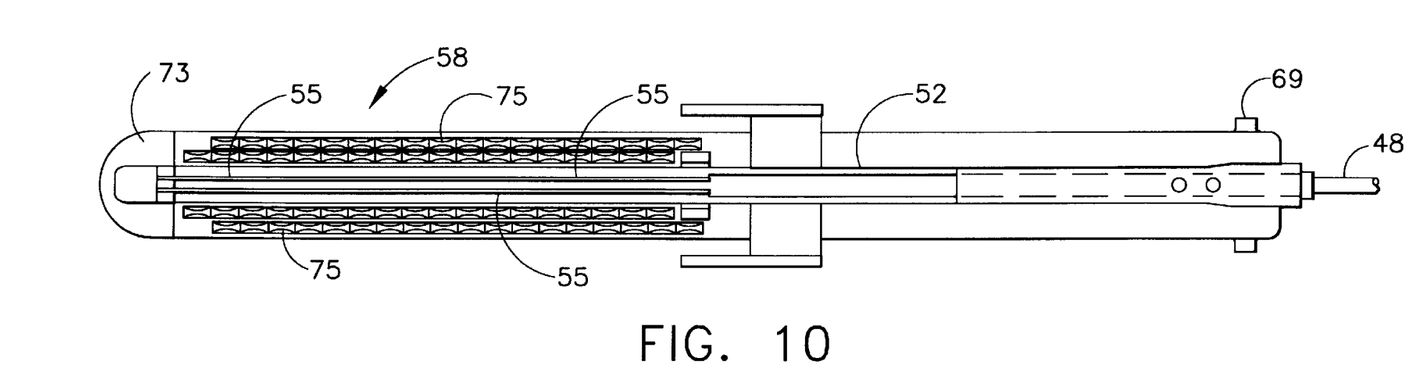
FIG. 10 is a bottom view of an anvil of an end effector according to one embodiment of the present invention.
Figure 11:
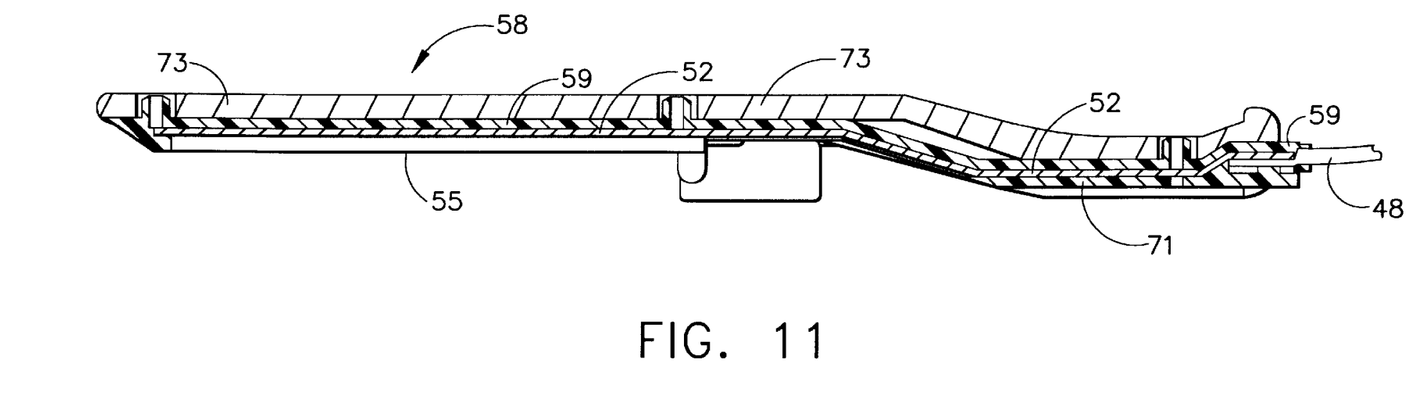
FIG. 11 is a cutaway side view of the anvil illustrated in FIG. 10.

FIG. 8 is a cutaway view of an end effector of an electrosurgical instrument according to one embodiment of the present invention. FIG. 9 is a cutaway view of a portion of a closure tube of an electrosurgical instrument according to one embodiment of the present invention. FIG. 10 is a bottom view of an anvil of an end effector according to one embodiment of the present invention. FIG. 11 is a cutaway side view of the anvil illustrated in FIG. 10. In FIGS. 8–11, Anvil base 58 supports electrode assembly 52 and includes staple forming slots 75. Electrode assembly 52 is electrically coupled to first electrode conductor 48 and to anvil electrodes 55. Anvil base 73 is insulated from electrode assembly 52 by anvil insulator 59. Channel 88 of end effector 57 supports staple cartridge 68, wedge guide 80 and wedge block assembly 82. Channel 88 extends into and, in one embodiment of the present invention illustrated in FIG. 9 is electrically coupled to closure tube 50 which, in turn is electrically coupled to second instrument electrode contact 43 to provide a return path for electrical energy coupled to end effector 57 through first instrument electrode contact 42. While outer tube 51 is not illustrated in the embodiments of the invention illustrated in FIGS. 8–11, it would be advantageous to use such an insulating tube to prevent short circuits. Closure tube 50 supports and encloses the proximal end of anvil 58, the proximal end of channel 88, firing rod 84, channel retainer 86 and at least a portion of wedge block assembly 82 and wedge guide 80. Anvil 58 opens and closes by, for example, pivoting around pivot pins 69.

In operation, trocar cannula 8 is used with a conventional trocar orbitor (not shown) to penetrate the wall of a body cavity such as, for example, the abdominal wall of a human being. After the body wall is penetrated, the obturator assembly is withdrawn from trocar cannula 8, and the cannula is used as an access portal for the passage of various endoscopic instruments to provide access to internal organs. Where the endoscopic instrument to be used is a cordless electrosurgical instrument such as electrosurgical instrument 16, electrosurgical adapter 14 may be attached to trocar cannula 8. Once electrosurgical adapter 14 is attached to trocar cannula 8 and electric cord 18 is attached to a suitable electrosurgical generator (not shown), electrosurgical trocar 11 may be used to provide electrosurgical energy to cordless electrosurgical instruments such as electrosurgical instrument 16.

When cordless electrosurgical instrument such as electrosurgical instruments 16 or 41 are inserted into a body cavity through, for example, electrosurgical trocar 11, end effector 57 passes through cannula 8 and into the body cavity while most of closure tube 50 remains in the trocar. Handle 72, which is outside of trocar 11, is manipulated by the surgeon to control the position of end effector 57.

A cordless bipolar electrosurgical instrument according to the present invention, such as electrosurgical instrument 16 of FIG. 7 may be used by inserting the cordless instrument into an appropriate electrosurgical trocar such as the electrosurgical trocar illustrated in FIG. 1. In the electrosurgical trocar illustrated in FIG. 1, electrosurgical energy is provided to instrument 16 by the interaction of contact 42 and contact 43 with the stator plates 28 and 29. The diameter of central aperture 19 generally corresponds with the outer diameter of closure tube 50, including outer tube 51, so that closure tube 50 slides through central aperture 19 and the interior of cannula tube 10. Contact 42 and contact 43, being raised above the surface of closure tube 50 and outer tube 51, will scrape against stator plates 28 and 29 as closure tube 50 passes through aperture 19. Compression member 32 will ensure that stator plates 28 and 29 maintain electrical contact with contacts 42 and 43, maintaining a good electrical connection between the stator plates in adapter 14 and the contact points on instrument 16. Electrical contact will be maintained so long as contacts 42 and 43 are positioned in central aperture 19 opposite stator plates 28 and 29. Electrical contact may be enhanced by using multiple contact points on instrument 16. With contacts 42 and 43 in contact with stator plates 28 and 29, electrosurgical energy may be supplied to electrosurgical trocar 11 through electric cord 18. The electrosurgical energy passes through conductors 36 and 38, stator tabs 26 and 27 and stator plates 28 and 29 into instrument 16 via contacts 42 and 43. Electrosurgical energy supplied to instrument 16 via contacts 42 and 43 may be supplied to end effector 57 via the circuit formed by first instrument electrode contact 42, conductor 48, electrode assembly 52, cartridge channel 88, closure tube 50 and second instrument electrode contact 43. This circuit is completed when tissue or other conductive tissue is grasped by end effector 57, providing a path from electrode assembly 52 to cartridge channel 88.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An electrosurgical instrument wherein said electrosurgical instrument comprises:

a) a handle;

b) an end effector operatively connected to said handle;

c) an elongated tube connecting said end effector to said handle;

d) a first electrical contact positioned on an outer surface of said elongated tube distal to said handle, wherein said first electrical contact is electrically connected to said end effector; and e) a second electrical contact positioned on an outer surface of said elongated tube distal to said handle wherein said second electrical contact is electrically connected to said end effector.

2. An electrosurgical instrument wherein said electrosurgical instrument comprises:

a) a handle including an actuator;

b) an end effector including first and second electrodes wherein said end effector comprises a first grasping element and a second grasping element;

c) an elongated, electrically conductive tube having an internal surface and an external surface, wherein said tube connects said end effector to said handle and includes a mechanism operatively connecting said end effector to said actuator;

d) first and second openings through said tube from said internal surface to said external surface;

e) an electrical insulator positioned in said first opening and surrounding said second opening;

f) a first electrical contact positioned at least partially in said second opening and extending above said outer surface of said elongated tube wherein said first electrical contact is electrically connected to said first electrode by an insulated wire positioned in said elongated tube;

g) a second electrical contact positioned on and extending above said outer surface of said elongated tube, wherein said elongated tube is electrically connected to said second electrode.

3. An electrosurgical instrument wherein said electrosurgical instrument comprises:

a) a handle means for holding said instrument;

b) an actuator means attached to said handle for opening and closing said end effector;

c) an end effector means for manipulating tissue, said end effector means including first and second electrodes wherein said end effector comprises;

d) an elongated, electrically conductive tube means for operatively connecting said handle to said end effector including a mechanism operatively connecting said end effector to said actuation trigger;

e) first and second openings through said elongated tube from said internal surface to said external surface;

f) an electrical insulator positioned in said first opening and surrounding said second opening;

g) a first electrical contact positioned at least partially in said second opening and extending above said outer surface of said elongated tube wherein said first electrical contact is electrically connected to said first electrode by an insulated wire positioned in said elongated tube;

h) a second electrical contact positioned on and extending above said outer surface of said elongated tube, wherein said elongated tube is electrically connected to said second electrode.

* * * * *